US008941646B2

(12) United States Patent
Inoue

(10) Patent No.: US 8,941,646 B2
(45) Date of Patent: Jan. 27, 2015

(54) ULTRASONIC DIAGNOSTIC APPARATUS AND ULTRASONIC IMAGE DISPLAY METHOD

(75) Inventor: Shinsuke Inoue, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 212 days.

(21) Appl. No.: 13/513,413

(22) PCT Filed: Jan. 13, 2011

(86) PCT No.: PCT/JP2011/050398
§ 371 (c)(1),
(2), (4) Date: Jun. 20, 2012

(87) PCT Pub. No.: WO2011/087035
PCT Pub. Date: Jul. 21, 2011

(65) Prior Publication Data
US 2012/0293507 A1    Nov. 22, 2012

(30) Foreign Application Priority Data

Jan. 15, 2010    (JP) ................................ 2010-006534
Sep. 10, 2010    (JP) ................................ 2010-202561

(51) Int. Cl.
*G06T 15/00*    (2011.01)
*A61B 8/08*    (2006.01)
(Continued)

(52) U.S. Cl.
CPC ................ *A61B 8/485* (2013.01); *A61B 8/483* (2013.01); *G01S 7/52042* (2013.01); *G01S 7/52071* (2013.01); *G01S 7/52074* (2013.01); *G01S 7/52084* (2013.01); *G01S 15/8993* (2013.01);
(Continued)

(58) Field of Classification Search
CPC .......... G06T 15/08; G06T 19/00; A61B 8/12; A61B 8/14; G06F 2210/41
USPC ........................................... 345/419; 600/443
See application file for complete search history.

(56) References Cited

U.S. PATENT DOCUMENTS 6,558,324 B1 *    5/2003    Von Behren et al. .......... 600/440
2005/0017972 A1 *    1/2005    Poole et al. ................... 345/424
(Continued)

FOREIGN PATENT DOCUMENTS

CN    101357077 A    2/2009
EP    1 938 754 A1    7/2008
(Continued)

OTHER PUBLICATIONS

Jan. 10, 2014 Chinese Office Action issued in Chinese Application No. 201180005195.3.
(Continued)

*Primary Examiner* — Hau Nguyen
*Assistant Examiner* — Ryan M Gray
(74) *Attorney, Agent, or Firm* — Oliff PLC

(57) ABSTRACT

Provided is an ultrasonic diagnostic apparatus which constructs a three-dimensional elastic image by separating elastic volume data and then performing volume rendering, and also provided is an ultrasonic image display method. The three-dimensional elastic image constructing unit separates the elastic volume data into a plurality of data sets on the basis of the elastic values and performs volume rendering on the separated elastic volume data sets, thereby constructing a three-dimensional elastic image.

14 Claims, 11 Drawing Sheets

(51) Int. Cl.
*G01S 7/52* (2006.01)
*G01S 15/89* (2006.01)
*G06T 15/08* (2011.01)
*G06T 19/00* (2011.01)
*A61B 8/00* (2006.01)

(52) U.S. Cl.
CPC ................. *G06T 15/08* (2013.01); *G06T 19/00* (2013.01); *A61B 8/465* (2013.01); *G01S 7/52073* (2013.01); *G06T 2210/41* (2013.01); *A61B 8/463* (2013.01)
USPC ........................................................ 345/419

(56) References Cited

U.S. PATENT DOCUMENTS

| | | | |
|---|---|---|---|
| 2005/0187473 A1* | 8/2005 | Boctor et al. | 600/437 |
| 2005/0273009 A1 | 12/2005 | Deischinger et al. | |
| 2006/0084870 A1* | 4/2006 | Kim et al. | 600/437 |
| 2006/0229513 A1 | 10/2006 | Wakai | |
| 2007/0112270 A1 | 5/2007 | Waki et al. | |
| 2009/0005679 A1* | 1/2009 | Dala-Krishna | 600/437 |
| 2009/0036749 A1 | 2/2009 | Freiburger et al. | |
| 2009/0251464 A1* | 10/2009 | Matsumoto | 345/424 |
| 2009/0264758 A1* | 10/2009 | Fujita et al. | 600/443 |

FOREIGN PATENT DOCUMENTS

| | | |
|---|---|---|
| JP | A-2006-288495 | 10/2006 |
| JP | A-2008-259605 | 10/2008 |
| JP | A-2009-34521 | 2/2009 |
| JP | B-4653938 | 12/2010 |
| WO | WO 2005/048847 A1 | 6/2005 |

OTHER PUBLICATIONS

Feb. 15, 2011 International Search Report issued in International Patent Application No. PCT/JP2011/050398.

Boctor et al., "Elasticity-Based Three Dimensional Ultrasound Real-Time Volume Rendering," *Proceedings of SPIE*, 2009, pp. 72612V-1-72612V-9, vol. 7261.

Extended European Search Report issued in European Application No. 11732905.2 dated Jul. 18, 2013.

* cited by examiner

ULTRASONIC DIAGNOSTIC APPARATUS AND ULTRASONIC IMAGE DISPLAY METHOD

FIELD OF THE INVENTION

The present invention relates to an ultrasonic diagnostic apparatus and an ultrasonic image display method that display a 3-dimensional elastic image presenting hardness and softness of biological tissues of an object using ultrasonic waves.

DESCRIPTION OF RELATED ART

An ultrasonic diagnostic apparatus is capable of transmitting ultrasonic waves to the inside of an object to be examined by an ultrasonic probe, obtaining and displaying a 3-dimensional tomographic image and a 3-dimensional elastic image on the basis of the reception signals received from biological tissues in the object.

At the time of superimposing and displaying a 3-dimensional tomographic image and a 3-dimensional elastic image, the setting of opacity is executed to facilitate recognition of the profile or volume of the hard region or soft region in the 3-dimensional elastic image (for example, Patent Document 1).

PRIOR ART DOCUMENT

Patent Document

Patent Document 1: JP-A-2008-259605

Though the above-described Patent Document 1 discloses the setting of opacity in a 3-dimensional tomographic image, separation of elastic volume data and execution of volume rendering are not disclosed therein. Thus in Patent Document 1, for example, a hard region and a soft region are mixed at the time of performing volume rendering in the process of constructing a 3-dimensional elastic image. As a result, when an operator intends to observe the hard region, the hard region could have been hidden by the soft region, which hinders the operator from recognizing the spread of the hard region.

The objective of the present invention is to construct a 3-dimensional elastic image by separating the elastic volume data at the time of performing volume rendering.

BRIEF SUMMARY OF THE INVENTION

In order to achieve the above-described objective of the present invention, the ultrasonic diagnostic apparatus comprises:

an ultrasonic probe having transducers that transmit/receive ultrasonic waves;

a transmission unit configured to transmit ultrasonic waves to an object via the ultrasonic probe;

a reception unit configured to receive the reflected echo signals from the object;

a 3-dimensional elastic image constructing unit configured to construct a 3-dimensional elastic image by performing volume rendering on the elastic volume data formed by the elasticity values based on the reflected echo signals; and a display unit configured to display the 3-dimensional elastic image, wherein the 3-dimensional elastic image constructing unit separates the elasticity volume data into plural sets of data on the basis of the elasticity values and performs volume rendering on the separated sets of elastic volume data so as to construct the 3-dimensional elastic image. In this manner, a 3-dimensional elastic image can be constructed by separating the elastic volume data at the time of performing volume rendering, and the operator can reciprocally recognize, for example the hard region and the soft region.

Also, the 3-dimensional elastic image constructing unit comprises an elastic volume data separating section configured to separate the elastic volume data into the hard region and the soft region on the basis of a predetermined reference value of the elastic volume data. The 3-dimensional elastic image constructing unit further comprises a first elasticity rendering calculation section configured to perform volume rendering on the elastic volume data which is equivalent to the hard region and a second elasticity rendering calculation section configured to perform volume rendering on the elasticity volume data which is equivalent to the soft region.

EFFECT OF THE INVENTION

In accordance with the present invention, it is possible to construct a 3-dimensional elastic image by separating the elastic volume data at the time of performing volume rendering.

BRIEF DESCRIPTION OF THE DIAGRAMS

Figure 8:
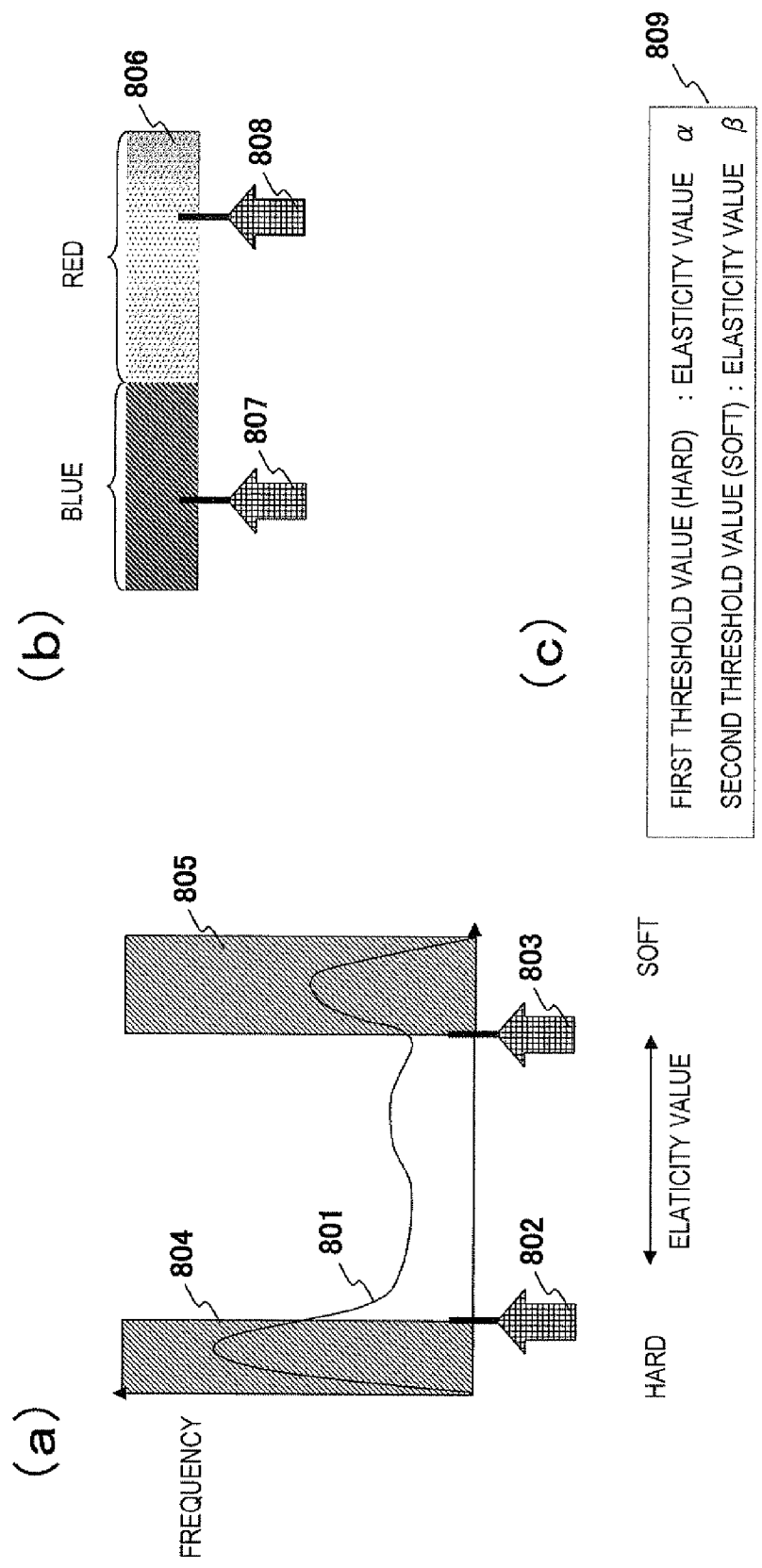
Figure 9:
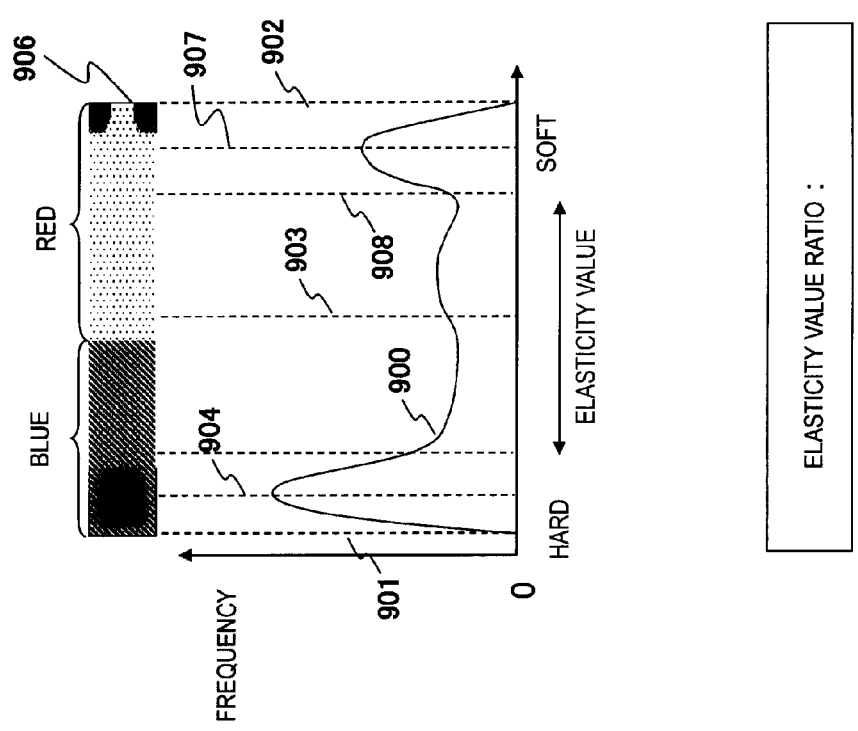
Figure 10:
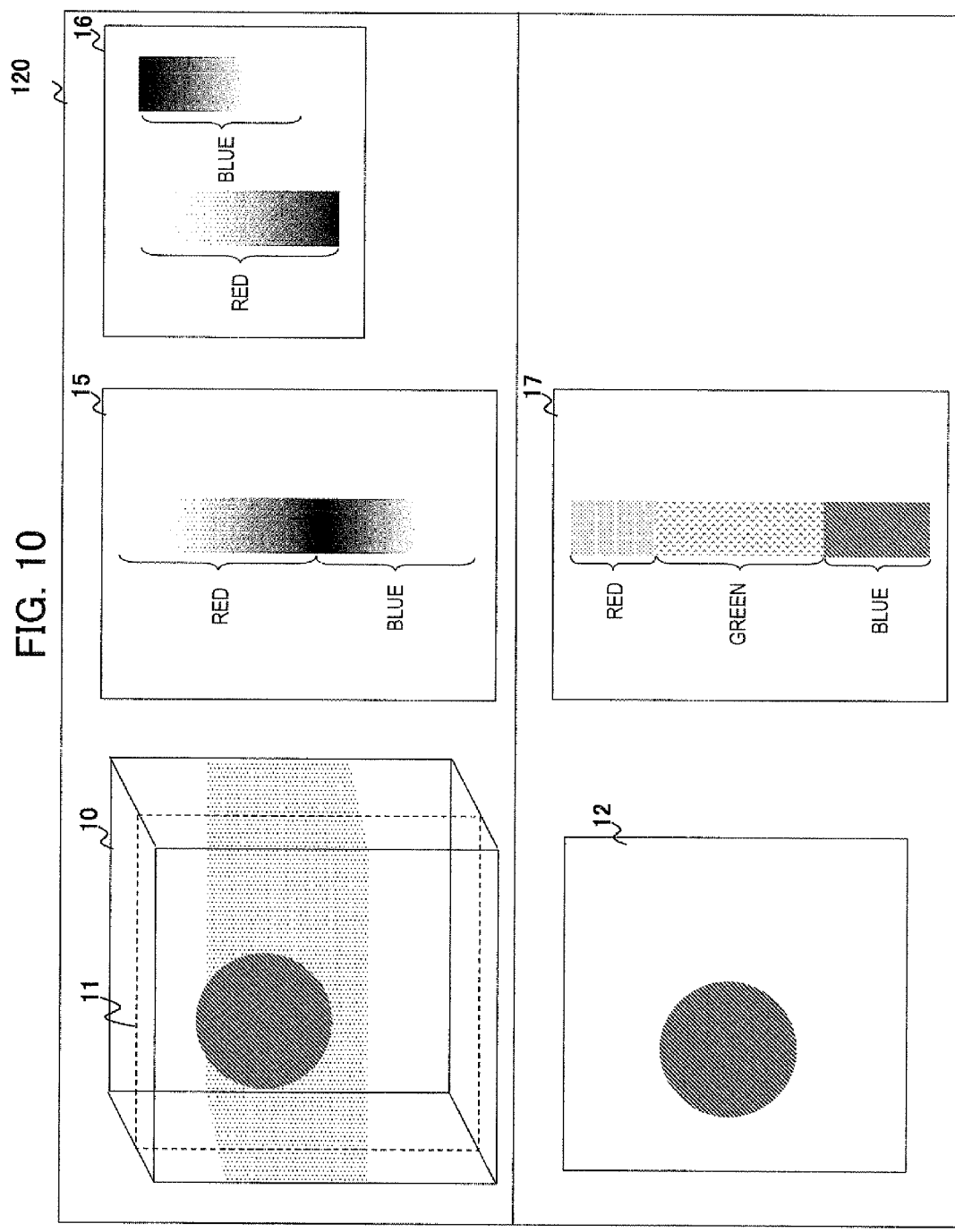
Figure 11:
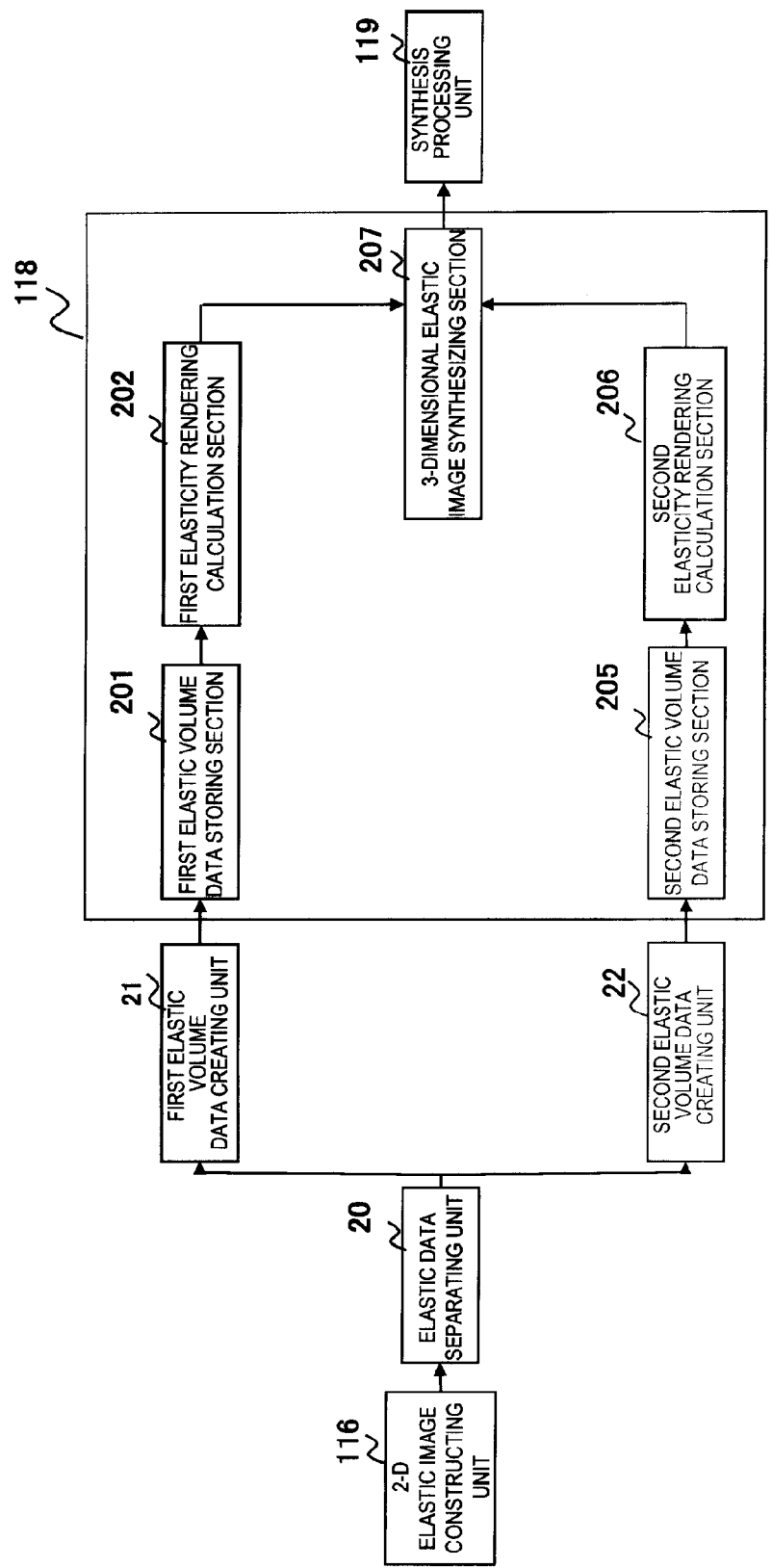

FIG. 8 shows a third embodiment of the present invention.
FIG. 9 shows a fourth embodiment of the present invention.
FIG. 10 shows a fifth embodiment of the present invention.
FIG. 11 shows a sixth embodiment of the present invention.

DETAILED DESCRIPTION OF THE INVENTION

Embodiment 1

An ultrasonic diagnostic apparatus 100 to which the present invention is applied will be described referring to FIG. 1.

Figure 1:
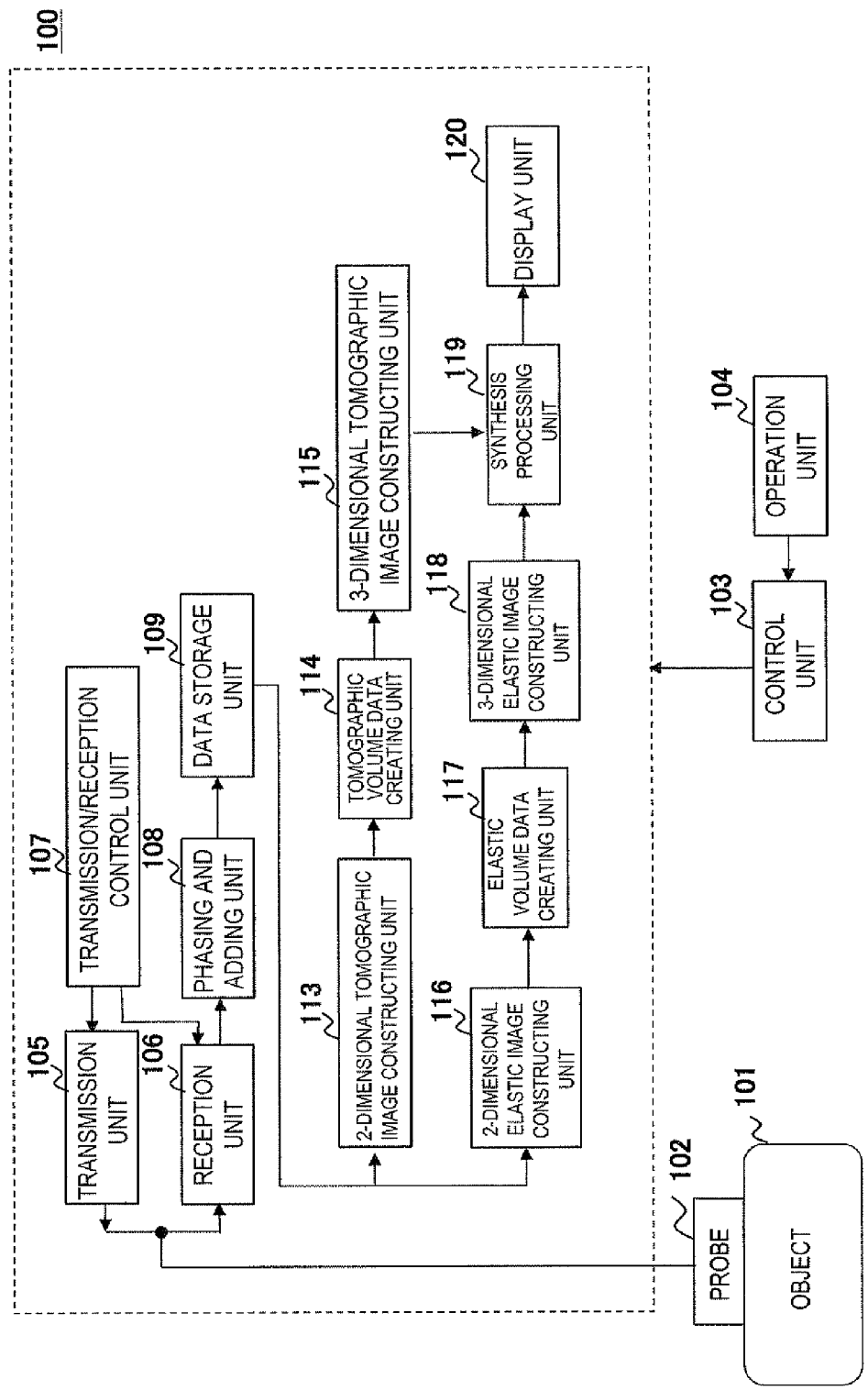
FIG. 1 is a block diagram showing the general configuration of the present invention.

As shown in FIG. 1, the ultrasonic diagnostic apparatus 100 is provided with an ultrasonic probe 102 to be used by applying to an object 101, a transmission unit 105 configured to repeatedly transmit ultrasonic waves to the object 101 at predetermined time intervals via the ultrasonic probe 102, a reception unit 106 configured to receive the echo signals reflected from the object 101, a transmission/reception control unit 107 configured to control the transmission 105 and the reception unit 106, and a phasing and adding unit 108 configured to execute phasing and adding on the reflected echoes received by the reception unit 106.

The ultrasonic probe 102 is provided with a plurality of transducers arrayed therein and has a function of transmitting/receiving ultrasonic waves to/from the object 101 via the transducers. The ultrasonic probe 102 is formed by a plurality of rectangle or fan-shaped transducers, capable of vibrating the transducers mechanically in the direction orthogonal to the array direction of the plurality of transducers and transmitting/receiving ultrasonic waves 3-dimensionally. The ultrasonic probe 102 may also comprise a plurality of transducers that are 2-dimensionally arrayed, which can electronically control the transmission and reception of ultrasonic waves.

The transmission unit 105 generates a transmitting pulse for activating a transducer of the ultrasonic probe 102 and generating an ultrasonic wave. The transmission unit 105 has a function of setting the convergent point of the transmitted ultrasonic waves at a certain depth. Also, the reception unit 106 amplifies the reflected echo signal received by the ultrasonic probe 102 by a predetermined gain and generates an RF signal, i.e. a reception signal. The ultrasonic transmission/reception control unit 107 controls the transmission unit 105 or the reception unit 106.

The phasing and adding unit 108 controls the phase of the RF signal which is amplified in the reception unit 106, and generates RF signal frame data (equivalent to RAW data) by forming an ultrasonic beam with respect to one or plural convergent points.

Further, the ultrasonic diagnostic apparatus 100 comprises a data storage unit 109 configured to store the RF signal frame data generated in the phasing and adding unit 108, a 2-dimensional tomographic image construction unit 113 configured to construct a 2-dimensional tomographic image on the basis of the RF signal frame data stored in the data storage unit 109, a tomographic volume data generating unit 114 configured to perform 3-dimensional coordinate conversion on the basis of the obtained position of the 2-dimensional tomographic image which is constructed in the 2-dimensional tomographic image construction unit 113 and generate tomographic volume data, a 3-dimensional tomographic image constructing unit 115 configured to perform volume rendering on the basis of the brightness and opacity of tomographic volume data and constructs a 3-dimensional tomographic image, a 2-dimensional elastic image construction unit 116 configured to construct a 2-dimensional elastic image on the basis of the plural sets of RF signal frame data stored in the data storage unit 109, an elastic volume data generating unit 117 configured to perform 3-dimensional coordinate conversion on the 2-dimensional elastic image constructed in the 2-dimensional elastic image constructing unit 116 on the basis of the obtained position of a 2-dimensional elastic image and generates elastic volume data, a 3-dimensional elastic image constructing unit 118 configured to perform volume rendering on the basis of the elastic value and the opacity of elastic volume data and construct a 3-dimensional elastic image, a synthesis processing unit 119 configured to synthesizes a 2-dimensional tomographic image and a 2-dimensional elastic image or a 3-dimensional tomographic image and a 3-dimensional elastic image, and a display unit 120 configured to display images such as a synthetic image synthesized in the synthesis processing unit 119 or a 2-dimensional tomographic image.

Also, the ultrasonic diagnostic apparatus 100 is provided with a control unit 103 configured to control the above-described components and an operation unit 104 for executing input of various information to the control unit 103. The operation unit 104 comprises devices such as a keyboard or a trackball.

The 2-dimensional tomographic image construction unit 113 performs signal processing such as gain compensation, log compression, detection, edge enhancement and filtering on the basis of the setting conditions in the control unit 103 by inputting the RF signal frame data output from the data storage unit 109, and constructs a 2-dimensional tomographic image.

The ultrasonic probe 2 is capable of measuring the transmitting and receiving directions ($\theta$, $\phi$) upon transmission and reception of ultrasonic waves, and the tomographic volume data generating unit 114 performs 3-dimensional conversion on a plurality of 2-dimensional tomographic images on the basis of the transmitting and receiving directions ($\theta$, $\phi$) that are equivalent to the obtaining position of a tomographic image, and generating tomographic volume data.

The 3-dimensional tomographic image constructing unit 115 performs volume rendering using the following equations (1)~(3) for constructing a 3-dimensional tomographic image from tomographic volume data.

$$C_{out}(i) = C_{out}(i-1) + (1 - A_{out}(i-1)) \cdot A(i) \cdot C(i) \cdot S(i) \quad (1)$$

$$A_{out}(i) = A_{out}(i-1) + (1 - A_{out}(i-1)) \cdot A(i) \quad (2)$$

$$A(i) = \text{Opacity}[C(i)] \quad (3)$$

C(i) is the luminance value of the i-th voxel that exists in the line of sight when a 3-dimensional tomographic image is viewed from a certain point on the created 2-dimensional projected plane. Cout(i) is the output pixel value. For example, when luminance values of N-voxels are lined up in the line of sight, luminance value Cout(N-1) obtained by integration from i=0 to N-1 is the pixel value to be ultimately output. Cout(i−1) indicates the integrated value up to the (i−1)-th luminance value.

Also, A(i) is the opacity of the i-th luminance value that exists in the line of sight, and is the tomographic opacity table which takes values of 0~4.0 as shown in the above equation (3). The tomographic opacity table determines the contribution rate of opacity on the output 2-dimensional projected plane (3-dimensional tomographic image) by referring to the opacity from the luminance value.

S(i) is the weighting component for shading to be computed by the slope which is acquired by luminance C(i) and the surrounding pixel values thereof. For example, when the light source coincides with the normal line of the plane which is centered on voxel "i", 1.0 is given for the maximum reflection, and when the light source and the normal line are orthogonal to each other, 0.0 is given which indicates accentuation effect.

Both Cout(i) and Aout(i) have 0 as the initial value. As shown in the equation (2), Aout(i) is integrated each time it passes through a voxel and converged to 1.0. Thus as shown in the above equation (1), when integrated value Aout(i−1) of up to the (i−1)-th opacity is about 1.0, the i-th and sequence luminance values C(i) will not be reflected on the output image.

The 2-dimensional elastic image constructing unit 116 measures the displacement from the plural sets of RF signal frame data stored in the data storage unit 109. Then the 2-dimensional elastic image constructing unit 116 calculates the elasticity value on the basis of the measured displacement, and constructs a 2-dimensional elastic image. The elasticity is any of the elastic information such as the strain, elasticity modulus, displacement, viscosity, and strain factor.

The elastic volume data generating unit 117 executes the 3-dimensional conversion on a plurality of 2-dimensional elastic images on the basis of the transmitting/receiving directions ($\theta$, $\phi$) equivalent to the obtained position of the 2-dimensional image, and generates the elastic volume data.

Figure 2:
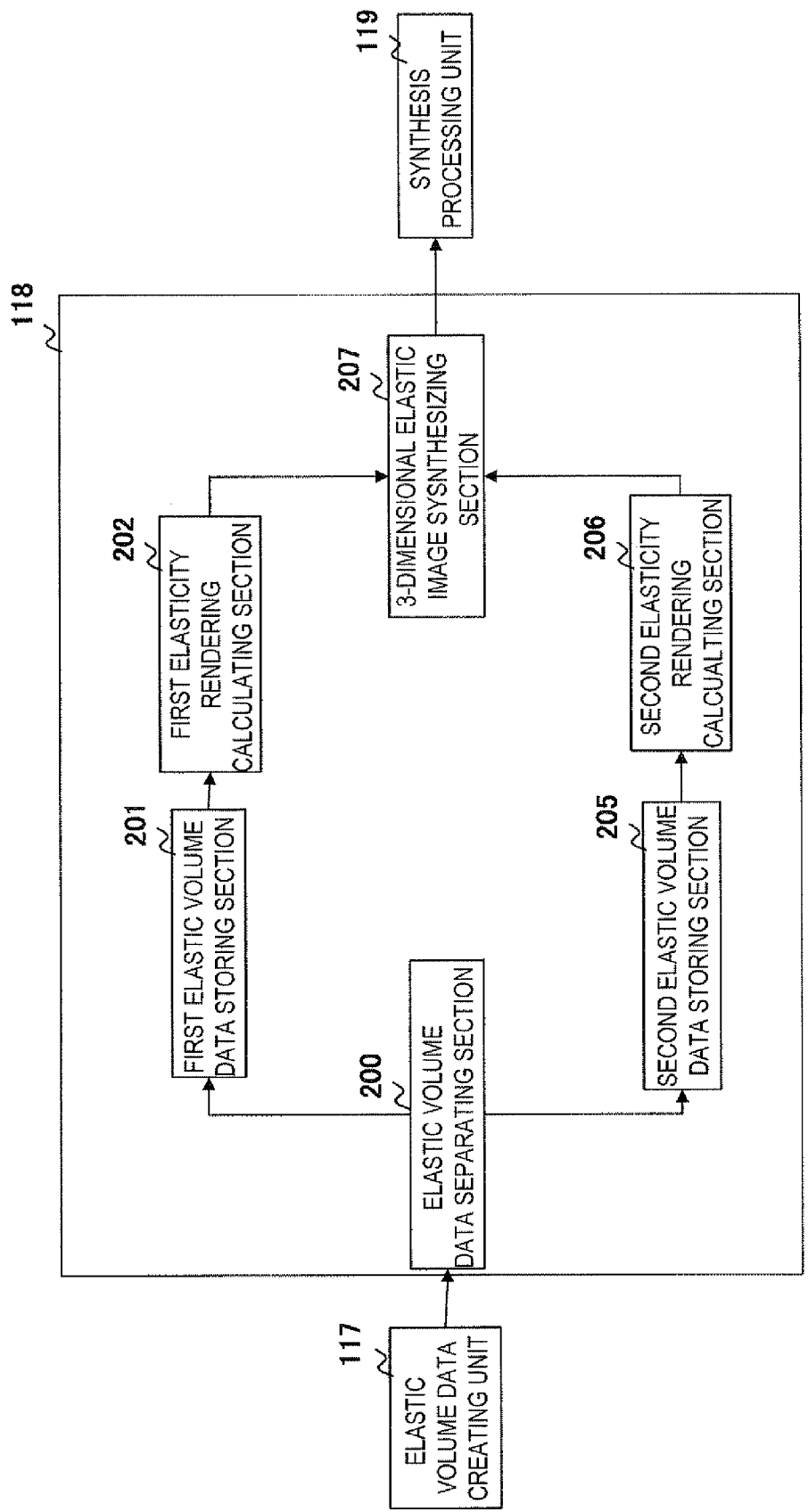
FIG. 2 shows a 3-dimensional elastic image constructing unit 118 in a first embodiment of the present invention.

The 3-dimensional elastic image constructing unit 118 separates the elastic volume data into plural sets on the basis of the elasticity value, performs volume rendering on the separated sets of elastic volume data, and constructs a 3-dimensional elastic image. The 3-dimensional elastic image constructing unit 118 will be described in concrete terms below referring to FIG. 2.

The 3-dimensional elastic image constructing unit 118 comprises an elastic volume data separating section 200 configured to separate elastic volume data into plural sets of elastic volume data on the basis of the elasticity value, a first elastic volume data storing section 201 configured to store one set of elastic volume data which is separated in the elastic volume data separating section 200, a first elasticity rendering calculation section 202 configured to perform volume rendering on the elastic volume data stored in the first elastic volume data storing section 201 and construct a 3-dimensional elastic image, a second elastic volume data storing section 205 configured to store the other set(s) of elastic volume data which is separated in the elastic volume data separating section 200, a second elasticity rendering calculation section 206 configured to perform volume rendering on the elastic volume data stored in the second elastic volume data storing section 205 and construct a 3-dimensional elastic image, and a 3-dimensional elastic image synthesizing section 207 configured to synthesize the plurality of 3-dimensional elastic images output from the first elasticity rendering calculation section 202 and the second elasticity rendering calculation section 206.

The elastic volume data separating section 200 will be described referring to FIG. 3. The elastic volume data separating section 200 separates the elastic volume data using the separation method shown in FIG. 3(*a*) or FIG. 3(*b*).

Figure 3:
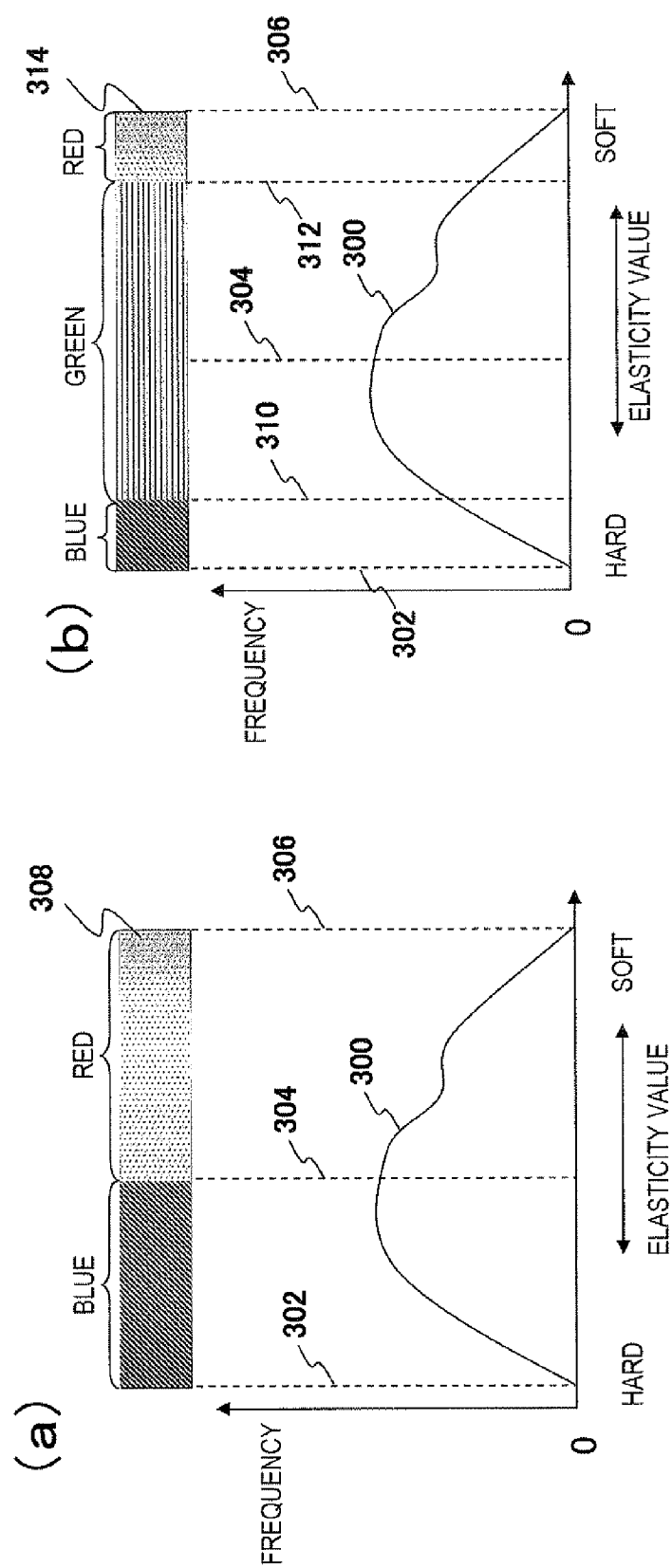
FIG. 3 shows an elastic volume data separating section 200 of the present invention.

In FIG. 3(*a*) and FIG. 3(*b*), a histogram showing the relationship between the elasticity value such as the strain or elasticity modulus and the frequency in the elastic volume data output from the elastic volume data generating unit 117 and lines for separating the elastic volume data are presented.

First, the separation method of elastic volume data shown in FIG. 3(*a*) will be described. A curve 300 is the histogram showing the relationship between the elasticity value of the elastic volume data and the frequency. A line 302 is a mark showing the hardest elasticity value from among the elastic volume data. A line 304 is a mark showing a predetermined reference value of the elastic volume data. A line 306 is a mark showing the softest elasticity value from among the elastic volume data. A color bar 308 shows that the elasticity values are separated into blue color and red color on the basis of a predetermined reference value of the elastic volume data. For example, in the elasticity values that are color coded as blue (red) color, the color bar 308 has a setting in which the higher the elasticity value is the darker the blue (red) color becomes and the lower the elasticity value is the lighter the blue (red) color becomes, though the gradation is not very clear since the diagram is in black and white.

The elastic volume data separating section 200 separates the elastic volume data into two sets of data of the hard region and the soft region on the basis of a predetermined reference value of the elastic volume data. A predetermined reference value is, for example any of the average value, the median or the mode value of the elastic volume data. The average value of the elastic volume data is the value wherein all elastic value of the elastic volume data are added and divided by the sum total of the elastic volume data sets. The median of the elastic volume data is the value which positions at the center between the hardest elasticity value and the softest elasticity value in the entire elasticity values of the elastic volume data. The mode value of the elastic volume data is the value which positions at the highest frequency in the histogram denoted by the curve 300.

An operator can select a predetermined reference value from among the average value, the median, the mode value, etc. of the elasticity values which constitute the elastic volume data, and sets the reference value on the basis of the selected value with respect to the elastic volume data separating section 200 by the control of the control unit 103 based on the operation on the operation unit 104. The elastic volume data separating section 200 separates the elastic volume data on the basis of the set reference value. In the initial setting, since the color coding width of the elasticity values by blue color and red color are the same width, the median of the elasticity volume data is set as the reference value in the elastic volume data separating section 200.

Also, the elastic volume data separating section 200 sets the elastic volume data on the left side which is equivalent to the hard region as blue color and the elastic volume data on the right side which is equivalent to the soft region as red color, on the basis of the line 304 indicating the predetermined reference value of the elastic volume data set as above. In this manner, a color value (blue color and red color) is given to the separated sets of elastic volume data respectively in accordance with the elasticity value.

The separation method of the elastic volume data shown in FIG. 3(*b*) will be described. The difference from the separation method in FIG. 3(*a*) is that the elastic volume data separating section 200 separates the elastic volume data into two sets of data of the hard region and the soft region while setting the position where the color other than blue changes to blue or the color other than red changes to red as the reference value.

The description on the curve 300, the line 302, the line 304 and the line 306 will be omitted since they are the same as in FIG. 3(*a*). A line 310 is a mark showing the position where the color other than blue changes to blue in the elastic volume data. A line 312 is a mark showing the position where the color other than red changes to red in the elastic volume data. A color bar 314 shows that the elasticity values are color coded into blue, red and green on the basis of predetermined values in the elastic volume data. For example, in the elasticity values that are color coded as blue (red, green) color, the color bar 314 has a setting in which the higher the elasticity value is the darker the blue (red, green) color becomes and the lower the elasticity value is the lighter the blue (red, green) color becomes, though the gradation is not very clear since the diagram is in black and white.

In the present embodiment, the position having the elasticity value which is softer than the hardest elasticity value by the portion of a predetermined value (for example, 20%) is set as the position where the color other than blue changes to blue. Also, the position having the elasticity value which is harder than the softest elasticity value by the portion of a predetermined value (for example, 20%) is set as the position where the color other than red changes to red.

The elastic volume data separating section 200 separates the elastic volume data having the harder elasticity value than the reference value on the basis of the reference value positioned at the softer elasticity value than the hardest elasticity value by the portion of a predetermined value. Then the elastic volume data separating section 200 gives blue color to the separated sets of elastic volume data. In other words, the elasticity values of the hard region (the elasticity values between the line 302 and the line 310) are colored in blue.

The elastic volume data separating section 200 separates the elastic volume data having the elasticity value softer than the reference elasticity value on the basis of the reference value positioned at the harder elasticity value than the softest elasticity value by the portion of a predetermined value. Then the elastic volume data separating section 200 gives red color to the separated sets of elastic volume data. In other words, the elasticity values of the soft region (the elasticity values between the line 312 and the line 306) are colored in red.

The color other than blue or the color other than red in this case is green. The region colored in green indicates the region having the average hardness in the elastic volume data.

Also, while the color information is given to the elastic volume data which is separated by the elastic volume data separating section 200 above, the color information may also be given to the separated sets of data by the elastic volume data generating unit 117 on the basis of the elasticity values at the time of generating the elastic volume data. The elastic volume data separating section 200 can also separate the elastic volume data based on the color information (RGB value) given in the elastic volume data generating unit 117.

The first elastic volume data storing section 201 stores the elastic volume data equivalent to the hard region (blue) which is separated by the elastic volume data separating section 200 on the basis of a predetermined reference value.

The first elasticity rendering calculation section 202 performs volume rendering on the elastic volume data equivalent to the hard region (blue) using the following equations (4)~(6), and creates a 3-dimensional elastic image of the hard region (blue).

$$E\text{out}(i) = R\text{out}(i-1) + (1 - A\text{out}(i-1)) \cdot A(i) \cdot E(i) \cdot S(i) \quad (4)$$

$$A\text{out}(i) = A\text{out}(i-1) + (1 - A\text{out}(i-1)) \cdot A(i) \quad (5)$$

$$A(i) = \text{Opacity}[E(i)] \quad (6)$$

E(i) is the i-th elasticity value that exists on the line of sight when a 3-dimensional elastic image is viewed from a certain point on the created 2-dimensional projected plane. Eout (i) is the output pixel value. For example, when elasticity values of N-voxels are lined up in the line of sight, integrated value Eout(N-1) obtained by integration of the elasticity values from i=0 to N-1 is the pixel value to be ultimately output. Eout(i-1) indicates the integrated value up to the (i-1)-th voxel. Also, A(i) is the opacity of the i-th elasticity value which exists in the line of sight, and is the elastic opacity table shown in the equation (6).

S(i) is the weighting component for shading to be computed by the slope which is acquired by elasticity value E(i) and the surrounding elasticity values thereof. For example, when the light source coincides with the normal line of the plane which is centered on voxel "i", 1.0 is given for the maximum reflection, and when the light source and the normal line are orthogonal to each other, 0.0 is given which indicates accentuation effect.

Both Eout(i) and Aout(i) have 0 as the initial value. As shown in the equation (5), Aout(i) is integrated each time it passes through a voxel and converged to 1.0. Thus as shown in the equation (4), when integrated value Aout(i-1) of the opacity of up to the (i-1)-th voxel is about 1.0, the i-th and subsequent voxel values E(i) will not be reflected on the output image.

The second elastic volume data storing section 205 stores the elastic volume data equivalent to the soft region (red) which is separated in the elastic volume data separating section 200 on the basis of a predetermined reference value.

The second elasticity rendering calculation section 206 performs volume rendering on the elastic volume data equivalent to the soft region (red) using the equations (4)~(6), and creates a 3-dimensional elastic image of the soft region (red).

The 3-dimensional elastic image synthesizing section 207 synthesizes the plurality of 3-dimensional elastic images output from the first elasticity rendering calculation section 202 and the second elasticity rendering calculation section 206. The synthesis processing unit 119 synthesizes the synthesized 3-dimensional elastic images and a 3-dimensional tomographic image. The 3-dimensional elastic image synthesizing section 207 will be described in concrete terms referring to FIG. 4~FIG. 6.

Figure 4:
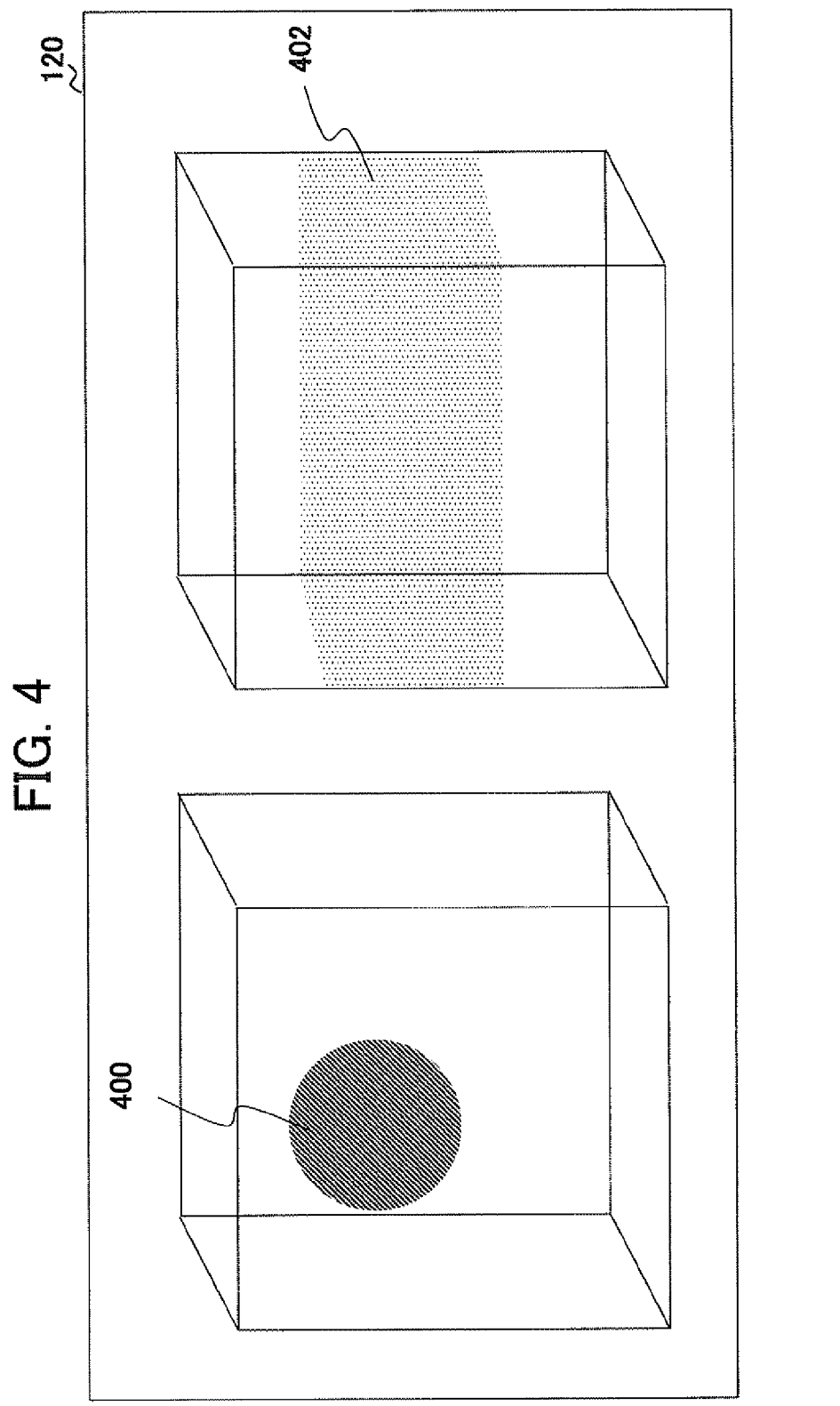
FIG. 4 shows a display pattern of a display unit 120 related to the present invention.

The 3-dimensional elastic image synthesizing section 207 is capable of synthesizing elastic images such that a 3-dimensional elastic image 400 of the hard region (blue) and a 3-dimensional elastic image 402 of the soft region (red) are juxtaposed and displayed on the display unit 120 as shown in FIG. 4. Therefore, the operator can compare and recognize the 3-dimensional elastic image 400 of the hard region (blue) and the 3-dimensional elastic image 402 of the soft region (red) respectively.

Figure 5:
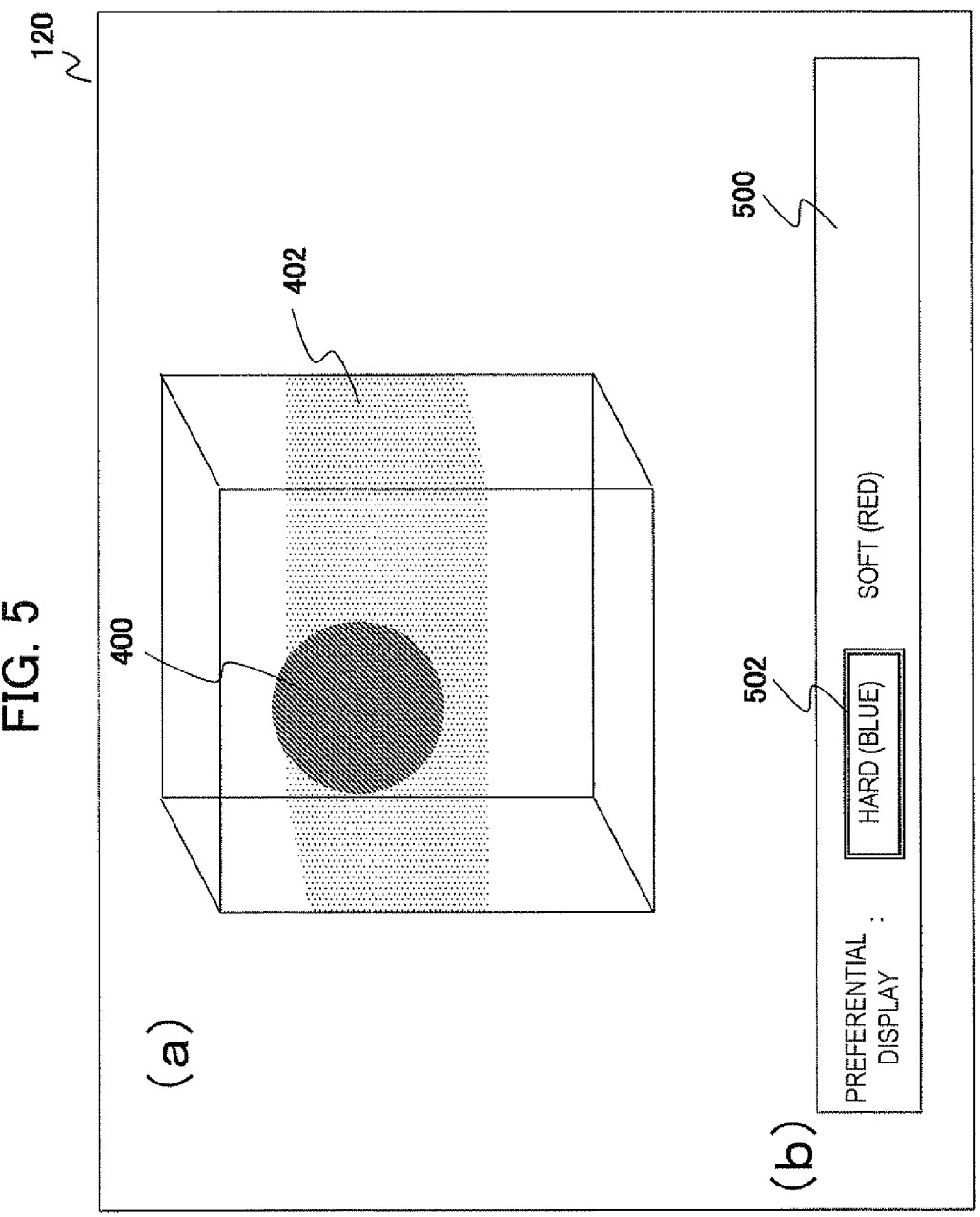
FIG. 5 shows a display pattern of a display unit 120 related to the present invention.

Also, the 3-dimensional elastic image synthesizing section 207 is capable of synthesizing the 3-dimensional elastic image 400 of the hard region (blue) and the 3-dimensional elastic image 402 of the soft region (red) such that the images are superimposed and displayed on the display unit 120 on a display pixel basis as shown in FIG. 5. On the display unit 120, a preferential display setting unit 500 is displayed, besides the synthesized 3-dimensional elastic image, for giving indication priority of the 3-dimensional elastic image 400 of the hard region (blue) or 3-dimensional elastic image 402 of the soft region (red).

On the preferential display setting unit 500, a selection mark 502 is displayed for showing that the hard region (blue) or the soft region (red) is selected. In FIG. 5, it is set so that the 3-dimensional elastic image 400 of the hard region (blue) is to be preferentially displayed.

In the case that the 3-dimensional elastic image 400 of the hard region (blue) is set to be preferentially displayed as shown in FIG. 5, the 3-dimensional elastic image synthesizing section 207 sets the 3-dimensional elastic image 402 of the soft region (red) to be displayed on the back surface and the 3-dimensional elastic image 400 of the hard region (blue) to be displayed on the front surface. In other words, the 3-dimensional elastic image of the hard region (blue) is superimposed on the 3-dimensional elastic image of the soft region (red) and displayed. In this manner, even when the 3-dimensional elastic image 400 of the hard region (blue) and the 3-dimensional elastic image 402 of the soft region (red) are synthesized, the operator can consistently confirm the hard region (blue).

Figure 6:
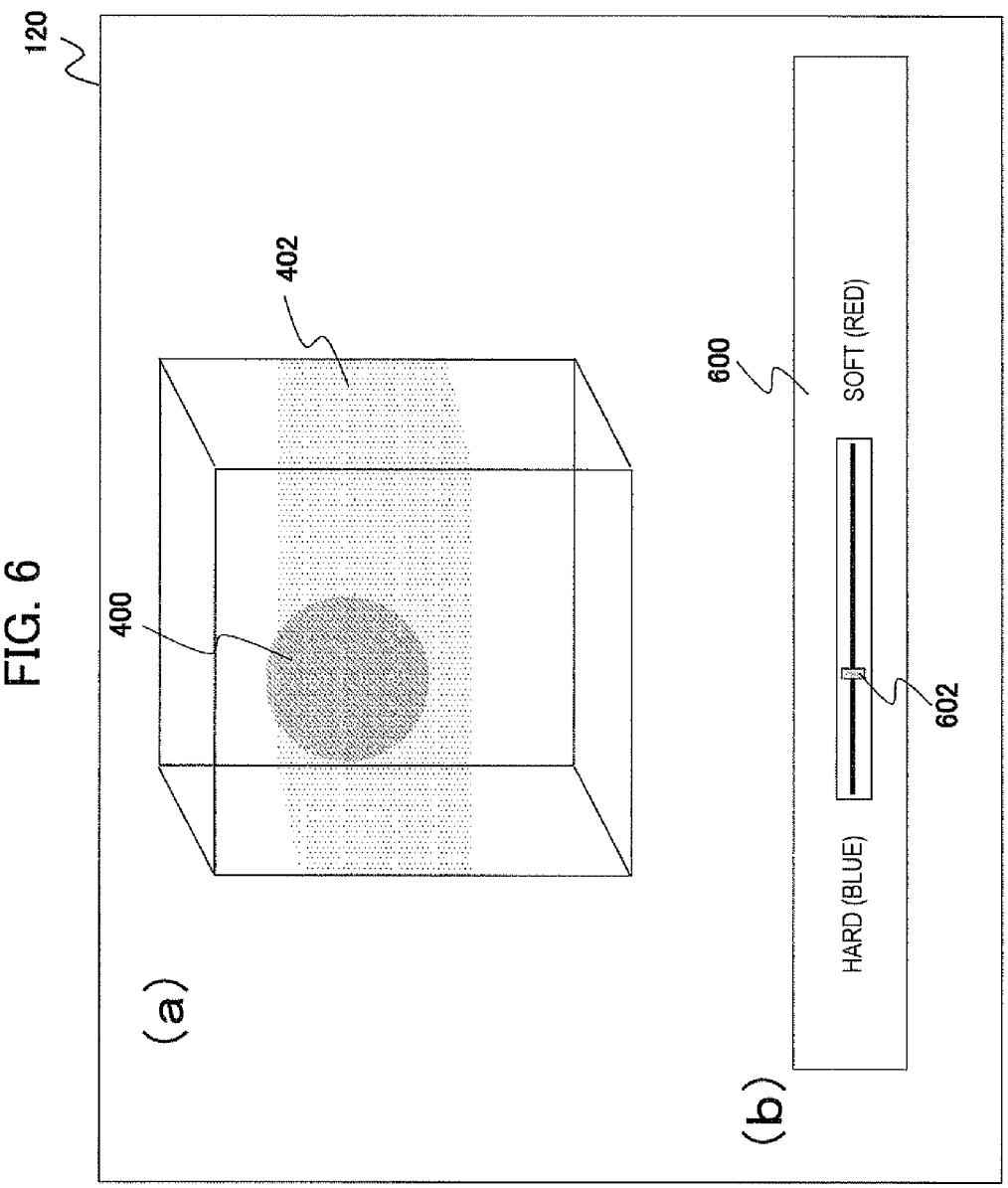
FIG. 6 shows a display pattern of a display unit 120 related to the present invention.
Figure 7:
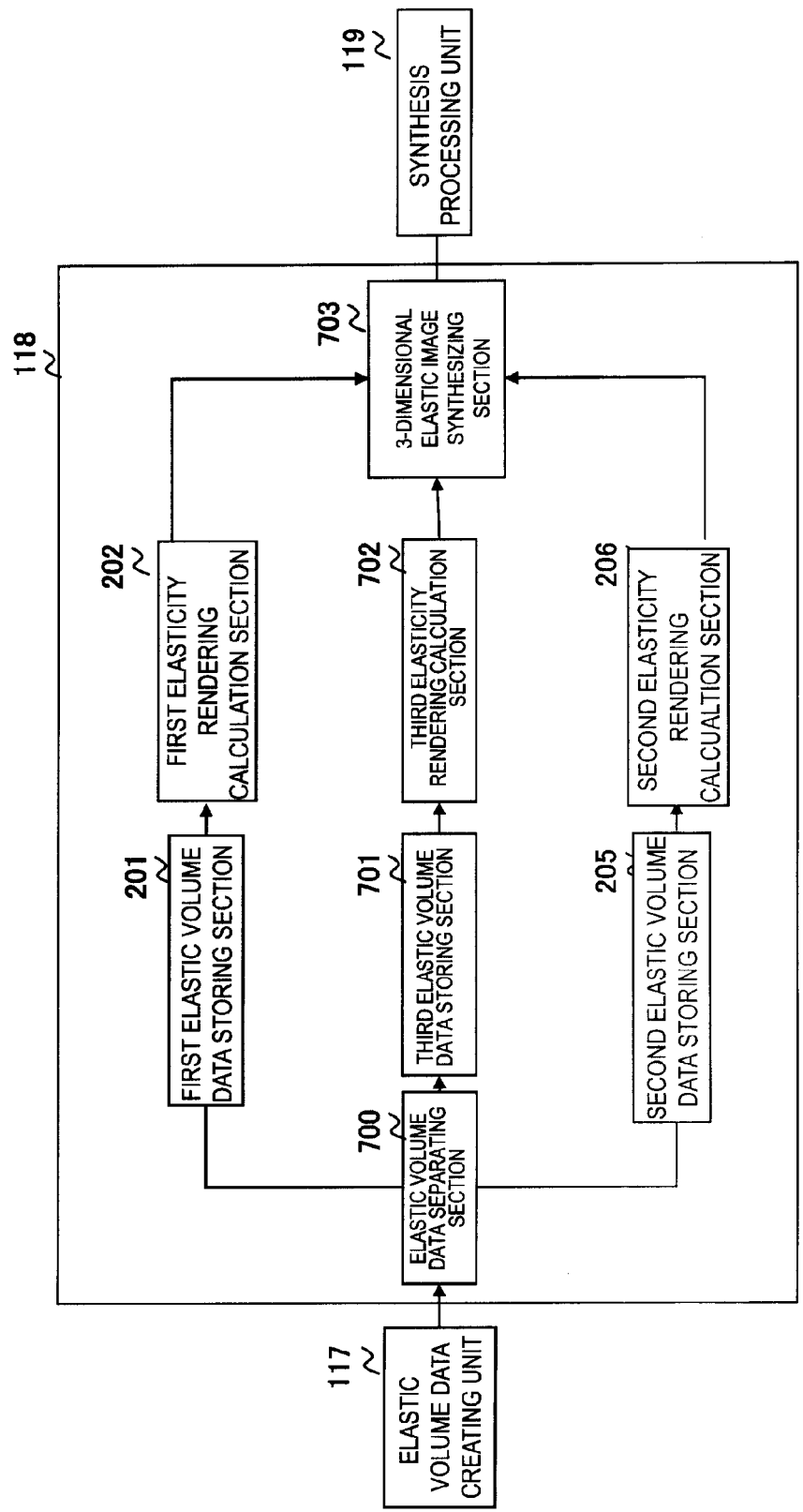
FIG. 7 shows the 3-dimensional elastic image constructing unit 118 in a second embodiment of the present invention.

Also, the 3-dimensional elastic image synthesizing section 207 is capable of synthesizing the elastic images by adding the 3-dimensional elastic image 400 of the hard region (blue) and the 3-dimensional elastic image 402 of the soft region (red) on the display pixel basis as shown in FIG. 6.

The 3-dimensional elastic image synthesizing section. 207 synthesizes the elastic images by adding the 3-dimensional elastic image 400 of the hard region (blue) and the 3-dimensional elastic image 402 of the soft region (red) with setting ratio α on a display pixel basis using the equations below. The setting ratio α is for setting the degree of translucence (translucency) of the 3-dimensional elastic image 400 of the hard region (blue) and the 3-dimensional elastic image 402 of the soft region (red) respectively, which is to be arbitrarily set by the control of the control unit 103 on the basis of the operation by the operation unit 104. The setting ratio α is 0 or more and 1 or less.

(Synthesized 3-dimensional elastic image $R$) =

$(1 - \alpha) \times$ (3-dimensional elastic image $R$ of hard region) +

$\alpha \times$ (3-dimensional elastic image $R$ of soft region)

(Synthesized 3-dimensional elastic image $G$) =

$(1 - \alpha) \times$ (3-dimensional elastic image $G$ of hard region) +

$\alpha \times$ (3-dimensional elastic image $G$ of soft region)

(Synthesized 3-dimensional elastic image $B$) =

$(1 - \alpha) \times$ (3-dimensional elastic image $B$ of hard region) +

$\alpha \times$ (3-dimensional elastic image $B$ of soft region)

Thus, the operator can reciprocally confirm the hardness information in the 3-dimensional elastic image 400 of the hard region (blue) and the hardness information in the 3-dimensional elastic image 402 of the soft region (red).

On FIG. 6, a ratio setting unit 600 for setting the setting ratio α and a ratio setting bar 602 for changing the setting ratio are displayed. When the ratio setting bar 602 is moved toward the left side from the center, the 3-dimensional elastic image synthesizing section 207 makes the value α small such that the 3-dimensional elastic image 400 of the hard region (blue) is emphasized with respect to the 3-dimensional elastic image 402 of the soft region (red). When the ratio setting bar 602 is moved toward the right side from the center, the 3-dimensional elastic image synthesizing section 207 makes the value of α large such that the 3-dimensional elastic image 402 of the soft region (red) is emphasized with respect to the 3-dimensional elastic image 400 of the hard region (blue).

For example, the ratio setting bar 602 is set at the center, the value of α becomes 0.5, and the 3-dimensional elastic image 400 of the hard region (blue) and the 3-dimensional elastic image of the soft region (red) are translucently displayed respectively. When the ratio setting bar 602 is set at the far left, the value of α becomes 0, and only the 3-dimensional elastic image 400 of the hard region (blue) is displayed. When the ratio setting bar 602 is set at the far right, the value of α becomes 1, and only the 3-dimensional elastic image 402 of the soft region (red) is displayed.

Though not shown in the diagram, the synthesis processing unit 119 is capable of displaying the 3-dimensional elastic image 400 of the hard region (blue) and the 3-dimensional elastic image 402 of the soft region (red) that are juxtaposed, superimposed or added and synthesized and a 3-dimensional tomographic image by synthesizing them respectively on a display pixel basis. The synthesis of the 3-dimensional elastic image 400, 3-dimensional elastic image 402 and a 3-dimensional tomographic image means, for example that the 3-dimensional elastic image 400 and the 3-dimensional elastic image 402 are made translucent and displayed over the 3-dimensional tomographic image, so that the hardness information of the 3-dimensional elastic image 400 and the 3-dimensional elastic image 402 and the tissue information of the 3-dimensional tomographic image can be confirmed on a reciprocal basis.

Switching of the display patterns of the display unit 120 shown in FIG. 4~FIG. 6 can be implemented under control of the control unit 103 on the basis of the operation of the operation unit 104, As described above, in accordance with the first embodiment of the present invention, it is possible to construct a 3-dimensional elastic image by separating the elastic volume data at the time of performs volume rendering, so that an operator can reciprocally confirm the soft region and the hard region.

Embodiment 2

Here, the second embodiment will be described referring to FIG. 1~FIG. 7. The difference from the first embodiment is that a 3-dimensional elastic image is constructed by separating the elastic volume data into a region having the average hardness (green) in addition to the hard region (blue) and the soft region (red) on the basis of predetermined reference values of the elastic volume data and performing volume rendering on the separated sets of elastic volume data. The 3-dimensional elastic image constructing unit 118 will be described in concrete terms using FIG. 7.

The 3-dimensional elastic image constructing unit 118 comprises an elastic volume data separating section 700 configured to separate elastic volume data into a hard region (blue), a soft region (red) and a region having average hardness (green) on the basis of the elasticity values, the first elastic volume data storing section 201 configured to store the elastic volume data equivalent to the hard region (blue) which is separated in the elastic volume data separating section 700, the first elastic rendering calculation section 202 configured to perform volume rendering on the elastic volume data stored in the first volume data storing section 201 and construct a 3-dimensional image, the second elastic volume data storing section 205 configured to store the elastic volume data equivalent to the soft region (red) which is separated by the elastic volume data separating section 700, a second elastic rendering calculation unit 206 configured to perform volume rendering on the elastic volume data stored in the second volume data storing section 205 and construct a 3-dimensional elastic image, a third volume data storing section 701 configured to store the elastic volume data equivalent to the region having average hardness (green) which is separated in the elastic volume data separating section 700, a third elastic rendering calculation section 702 configured to perform volume rendering on the elastic volume data stored in the third volume data storing section 701 and construct a 3-dimensional image, and a 3-dimensional elastic image synthesizing section 703 configured to synthesize a plurality of 3-dimensional elastic images output from the first elastic rendering calculation section 202, the second elastic rendering calculation section 206 and the third elastic rendering calculation section 702.

The elastic volume data separating section 700 separates elastic volume data using the separation method of the elastic volume data shown in FIG. 3(*b*). The elastic volume data separating section 700 separates the elastic volume data into three sets of the hard region, soft region and the region having the average hardness, on the basis of the reference values which are set at the position where the color other than blue changes to blue and at the position where the color other than red changes to red.

The description of the first elastic volume data storing section 201, the first elastic rendering calculation section 202, the second elastic volume data storing section 205 and the second elastic rendering calculation section 206 will be omitted, since they are already described in the first embodiment.

The elastic volume data separating section 700 separates the elastic volume data, on the basis of a first reference value which is at the position of the elasticity value which is softer than the hardest elasticity value by the portion of a predetermined value and a second reference value which is at the position of the elasticity value which is harder than the softest elasticity value by the portion of a predetermined value, of the region having the average hardness which is equivalent to the values between the first reference value and the second reference value. Then the elastic volume data separating section 700 gives green color to the separated set of elastic volume data. That is, green color is given to the elasticity value of the region having the average hardness (the elasticity values between the line 310 and the line 312).

The third elastic volume data storing section 701 stores the elastic volume data equivalent to the region having the average hardness (green) which is separated in the elastic volume data separating section 701 on the basis of predetermined reference values.

The third elastic volume rendering calculation section 703 performs volume rendering on the elastic volume data equivalent to the region having the average hardness (green) using the above equations (4)~(6), and creates a 3-dimensional elastic image of the region having the average hardness (green).

The 3-dimensional elastic image synthesizing section 703 synthesizes the plurality of 3-dimensional elastic images output from the first elastic volume rendering calculation section 202, the second elastic volume rendering calculation section 206 and the third elastic volume rendering calculation section 702. The concrete description of the 3-dimensional elastic image synthesizing section 703 will be omitted since it is the same as the display patterns shown in FIG. 4~FIG. 6 except for replacing two image-synthesizing parameters with three image-synthesizing parameters.

As described above, in accordance with the second embodiment of the present invention, a 3-dimensional elastic image can be constructed by separating the elastic volume data at the time of performing volume rendering, and an operator can reciprocally confirm the hard region, the soft region and the average-hardness region.

While elastic volume data is separated into two sets in the first embodiment and into three sets in the second embodiment, the elastic volume data may also be separated into four or more sets of data.

Embodiment 3

Here, the third embodiment will be described referring to FIG. 8. The difference from the first embodiment and the second embodiment is that an operation unit 104 which sets a threshold value of elasticity values is comprised, and that the 3-dimensional elastic image constructing unit 118 constructs a 3-dimensional elastic image by further separating the elastic volume data which is separated into the hard region and the soft region and converting the voxel value of the separated sets of elastic volume data into the voxel value which is greater than the original voxel value at the time of performing volume rendering.

FIGS. 8(a)~(c) show the patterns for setting the threshold value for separating elastic volume data. These patterns are displayed on the display unit 120. The operator sets the threshold value for separating the elastic volume data via the operation unit 104. Then the 3-dimensional elastic image constructing unit 118 constructs a 3-dimensional elastic image by separating the elastic volume data on the basis of the set threshold value and performing volume rendering on the separated sets of elastic volume data.

The elastic volume data is separated into the elastic volume data equivalent to the hard region and the elastic volume data equivalent to the soft region by the elastic volume data separating section 200, and the elastic volume data equivalent to the hard region is stored in the first elastic volume data storing section 201 and the elastic volume data equivalent to the soft region is stored in the second elastic volume data storing section 205.

The operator sets a first threshold value with respect to the elastic volume data equivalent to the hard region and a second threshold value with respect to the elastic volume data equivalent to the soft region via the operation unit 104.

As shown in FIG. 8(a), a first threshold value 802 and a second threshold value 803 are set in the histogram 801 showing the relationship between the elasticity value such as the strain or elasticity modulus and the frequency. The operator can set the first threshold value and the second threshold value, for example so as to include the elasticity value which becomes the peak in the histogram 801. The control unit 103 detects elasticity value α which corresponds to the first threshold value 802 and elasticity value β which corresponds to the second threshold value 803.

The control unit 103 transmits the detected elasticity value α which corresponds to the first threshold value 802, to the first elastic rendering calculation section 202. The first elastic rendering calculation section 202 extracts an elastic volume data 804 from the elastic volume data equivalent to the hard region which is stored in the first elastic volume data storing section 201 while setting the voxel value having the elasticity value which is harder than the elasticity value a corresponding to the set first threshold value 802 as 255 and the voxel value having the elasticity value which is softer than the elasticity value α as 0. The first elastic rendering calculation section 202 performs volume rendering with respect to the extracted elastic volume data 804.

The advantage of converting the voxel value having the elasticity value which is harder than the elasticity value a into the voxel value which is larger than the original voxel value will be described. The elasticity values of the elastic volume data 804 in which only the hard region is extracted are small values as shown in FIG. 8(a). Since A(i) and S(i) to be multiplied by elasticity value E(i) in the equation (4) is 1.0 or less, the calculation result of the second term in the equation (4) will be the value of E(i) or less. Therefore, when E(i) is a small value, the rendering calculation makes the value an even smaller value which is difficult to be displayed. Given this factor, by converting the voxel value having the elasticity value which is harder than the elasticity value a into the voxel value which is greater than the original value, the calculation can be performed in the suitable manner for volume rendering. While the case that the voxel value is converted into 255 is exemplified in the present embodiment, any voxel value which is appropriate enough to be recognized as a hard region may be used.

Also, the control unit 103 transmits the elasticity value β which corresponds to the detected second threshold value 803 to the second elastic rendering calculation section 206. The second elastic rendering calculation section 206 extracts elasticity volume data 805 having the elasticity value which is softer than the elasticity value corresponding to the set second threshold value 803 from the elastic volume data equivalent to the soft region stored in the second elastic volume data storing section 205 and performs volume rendering. While the soft region usually has a large elasticity value, volume rendering may be executed after converting the elasticity value into an arbitrary large value in the same manner as the hard region.

In other words, the elastic volume data 804 which is harder than the first threshold value 802 is extracted from the elastic volume value equivalent to the hard region, for constructing a 3-dimensional elastic image. From the elastic volume data equivalent to the soft region, the elastic volume data 805 which is softer than the second threshold value 803 is extracted for constructing a 3-dimensional elastic image.

Also as shown in FIG. 8(*b*) a first threshold value 807 and a second threshold value 808 can be set to a color bar 806 which sets colors on elastic volume data. The control unit 103 detects the elasticity value α or the elasticity value β which correspond to the hue of the color bar 806. Also as shown in FIG. 8(*c*), the elasticity value α or the elasticity value β such as the strain or elasticity modulus may also be input directly in the operation unit 104. The control unit 103 detects the elasticity value α or the elasticity value β. The description on the volume rendering process in the first elastic rendering calculation section 202 and the second elastic rendering calculation section 206 using the elasticity value α or the elasticity value β detected by the control unit 103 will be omitted since it is the same as described above.

As described above, in accordance with the third embodiment of the present invention, a 3-dimensional elastic image can be constructed by further separating the elasticity volume data equivalent to the hard region or the elastic volume data equivalent to the soft region on the basis of the threshold value and extracting a desired set of elastic volume data. Therefore, it is possible to construct a 3-dimensional elastic image of the hardness which is necessary for diagnosis, by eliminating the 3-dimensional elastic image of the unnecessary hardness.

Embodiment 4

Here, the fourth embodiment will be described referring to FIG. 9. The difference from the first~third embodiment is that a 3-dimensional elastic image is constructed by setting a threshold value of an elasticity value on the basis of the characteristic of the histogram of the elasticity value and performing volume rendering with respect to the elastic volume data which is separated on the basis of a threshold value.

The elastic volume data separating section 200 separates the elastic volume data into two sets of the hard region and the soft region on the basis of a predetermined reference value of the elastic volume data.

In FIG. 9, a histogram 900 showing the relationship between the elasticity value such as the strain or the elasticity modulus and the frequency in the elastic volume data which is output from the elastic volume data generating unit 117 and a plurality of lines for separating the elastic volume data are displayed.

A line 901 is a mark indicating the hardest elasticity value among the elastic volume data. A line 902 is a mark indicating the softest elasticity value among the elastic volume data. A line 903 is a mark indicating the average value in the elastic volume data. A line 904 is a mark indicating the mode value in the elastic volume data.

The elastic volume data separating section 200 separates the elastic volume data on the basis of the mode value in the histogram 900 of the elastic volume data. For example, the elasticity-value range of the elastic volume data is set using the mode value±predetermined value. The predetermined value can be set by the operator via the operation unit 104. The predetermined value can also be set using the statistics based on the histogram 900. The first elastic rendering calculation section 202 performs volume rendering with respect to the elastic volume data within the set elasticity-value range for constructing a 3-dimensional elastic image.

Also, a second elasticity-value range from the line 902 to the line 908, based on the line 907, indicating a second mode value which is the next highest mode value that follows the highest mode value may be separated as shown in FIG. 9. The second elastic rendering calculation section 206 performs volume rendering with respect to the elastic volume data of the second elasticity-value range for constructing a 3-dimensional elastic image. Since the second elasticity-value range is equivalent to the region which is softer than the average value, it is colored in red using the color bar 906.

While the pattern up to the second mode value is described in the present embodiment, a third and fourth mode values may also be used. Also, the ratio between the elasticity value of the mode value and the elasticity value equivalent to the second mode value can be calculated and displayed on the display unit 120.

Embodiment 5

Here, the fifth embodiment will be described referring mainly to FIG. 10. The difference from the first~fourth embodiments is that the 3-dimensional elastic image constructing unit 118 performs coloring in three dimensions on the 3-dimensional elastic image based on the elastic volume data which is separated into the hard region and the soft region using the color bar for 3-dimensional elastic images.

On the display unit 120, a 3-dimensional elastic image 10 which is constructed in the 3-dimensional elastic image constructing unit 118 and a 2-dimensional elastic image 12 which is constructed in the 2-dimensional elastic image constructing unit 116 are displayed. On the 3-dimensional elastic image 10, a cross-section mark 11 indicating the cross section of the 2-dimensional elastic image 12 is displayed.

Also, color bars 15 and 16 for 3-dimensional elastic images to set the coloring on 3-dimensional elastic images and a color bar 17 for 2-dimensional elastic images to set the coloring on a 2-dimensional elastic image are displayed on the display unit 120. The color bar 15 for 3-dimensional elastic images shows the pattern of one color bar and the color bar 16 for 3-dimensional elastic images shows the pattern of two color bars, of which one is to be displayed on the display unit 120. The color bars 15 and 16 for 3-dimensional elastic images and the color bar 17 for a 2-dimensional elastic image are set to have different coloring features. The color bars 15 and 16 for 3-dimensional elastic images are set to display 3-dimensional elastic images in 3-dimensions. The color bar 17 for a 2-dimensional elastic image is set to clearly display the distribution of elasticity values in the 2-dimensional elastic image which is formed by the elasticity values based on the reflected echo signals.

The elasticity volume data is separated into the elastic volume data equivalent to the hard region and the elastic volume data equivalent to the soft region by the elastic volume data separating section 200. Then the 3-dimensional elastic image constructing unit 118 (elastic volume data separating section 200) gives the color which indicates the hardness (blue) and the color which indicates the three-dimensionality (black) to the elasticity volume data equivalent to the hard region on the basis of the color bars 15 and 16 for 3-dimensional elastic images, and gives the color which indicates the softness (red) and the color which indicates the 3-dimensionality (black) to the elastic volume data equivalent to the soft region.

The color bars 15 and 16 for 3-dimensional elastic images are set to emphasize the black color as the pixel value after the rendering decreases, and to emphasize the blue (red) color as the pixel value increases. This is to exert the effect in the equation (4) that the closer $S(i)$ is to 1.0 the lighter the color changes and the closer $S(i)$ is to 0.0 the darker the color changes.

While the information of hardness and shading is given to the vertical axis of the color bars 15 and 16 for 3-dimensional elastic images in the above description, the information to be given to color bars for 3-dimensional elastic images may be two-dimensionally separated into the hardness for the vertical axis and the shading for the lateral axis.

In this manner, a 3-dimensional elastic image is three-dimensionally displayed by separating the elastic volume data into the hard region and the soft region and coloring them by the color bars 15 and 16 for 3-dimensional elastic images.

Also, the color bar 17 for 2-dimensional elastic images converts the 2-dimensional elastic image from the color codes of the light's three primary colors, i.e. red, green and blue into the colors which indicate the hardness or the softness. The color bar 17 for 2-dimensional elastic images indicates the soft region of biological tissues in red, the hard region in blue and the intermediate hardness thereof in green. Though not shown in the diagram, there is no borderline between red color and green color as well as between green color and blue color, and these colors are connected by gradation. The 2-dimensional elastic image is set so that the elasticity values therein can be recognized on the basis of the colors set by the color bar 17 for 2-dimensional elastic images. Thus, the distribution of elasticity values in the 2-dimensional elastic image can be clearly displayed.

In this manner, 3-dimensional elastic images and a 2-dimensional elastic image which are suitable for diagnosis can be displayed, since the coloring features are differentiated in the color bars 15 and 16 for 3-dimensional elastic image and the color bar 17 for 2-dimensional elastic images.

Embodiment 6

Here, the sixth embodiment will be described referring to FIG. 11. The difference from the first~fifth embodiments is that an elastic data separating unit 20 is provided which separates the elasticity data into plural hardness regions based on the elasticity values in the 2-dimensional elastic image output from the 2-dimensional elastic image constructing unit 116.

While the elastic volume data separating section 200 separates the elastic volume data output from the elastic volume data generating unit 117 into plural sets of elastic volume data in the first~fifth embodiments, the elastic volume data may also be separated before being generated as shown in FIG. 11 so as to generate the elastic volume data from the separated sets of elastic data.

The elastic data separating unit 20 separates the elastic data into plural hardness regions on the basis of the elasticity values of the 2-dimensional elastic image output from the 2-dimensional elastic image constructing unit 116. A first elastic volume data generating unit 21 generates elastic volume data using the 2-dimensional elastic image from one set of data which is separated by the elastic data separating unit 20, and a second elastic volume data generating unit 22 generates elastic volume data using the other 2-dimensional elastic image from the data which is separated by the elastic data separating unit 20. The separation method of the elastic data separating unit 20 is the same as in the first~fifth embodiments.

DESCRIPTION OF REFERENCE NUMERALS

100: ultrasonic diagnostic apparatus
102: ultrasonic probe
103: control unit
104: operation unit
105: transmission unit
106: reception unit
107: transmission/reception control unit
108: phasing and adding unit
109: data storage unit
113: 2-dimensional tomographic image constructing unit
114: tomographic volume data generating unit
115: 3-dimensional elastic image constructing unit
116: 2-dimensional elastic image constructing unit
117: elastic volume data generating unit
118: 3-dimensional elastic image constructing unit
119: synthesis processing unit
120: display unit

The invention claimed is:

1. An ultrasonic diagnostic apparatus comprising:
an ultrasonic probe provided with transducers configured to transmit/receive ultrasonic waves;
a transmitter configured to transmit ultrasonic waves to an object to be examined via the ultrasonic probe;
a receptor configured to receive reflected echo signals from the object;
an elastic volume data generator for generating elastic volume data by using the reflected echo signals; and
a 3-dimensional elastic image constructor configured to construct a 3-dimensional elastic image by performing volume rendering on the elastic volume data; and
a display configured to display the 3-dimesnional elastic image,
wherein the 3-dimensional elastic image constructor comprises:
an elastic volume data grouper for grouping the elastic volume data into a first set of elastic volume data of a hard region and a second set of elastic volume data of a soft region by using an elastic value,
a first elastic renderer for volume rendering a first set of elastic volume data to produce a first 3-dimensional elastic image of the hard region,
a second elastic renderer for volume rendering a second set of elastic volume data to produce a second 3-dimensional elastic image of the soft region,
a 3-dimensional elastic image synthesizer for synthesizing the first 3-dimensional elastic image and the second 3-dimensional elastic image,
wherein the 3-dimensional elastic image synthesizer synthesizes the first 3-dimensional elastic image and the second 3-dimensional elastic image to thereby superimpose the first 3-dimensional elastic image and the second 3-dimensional elastic image onto the display screen.

2. The ultrasonic diagnostic apparatus according to claim 1, wherein the elastic volume data grouper is configured to separate the elastic volume data into the hard region and the soft region on the basis of a predetermined reference value of the elastic volume data.

3. The ultrasonic diagnostic apparatus according to claim 2, wherein the predetermined reference value is any of the average value, the median or the mode value of the elastic volume data.

4. The ultrasonic diagnostic apparatus according to claim 2, wherein the elastic volume data grouper sets the elastic volume data equivalent to the hard region to be colored in blue and the elastic volume data equivalent to the soft region to be colored in red, on the basis of the predetermined reference value.

5. The ultrasonic diagnostic apparatus according to claim 1, wherein the elastic volume data grouper is configured to separate the elastic volume data into the elastic volume data having the elasticity value which is harder than the elasticity value of the reference value on the basis of the reference value positioned at the elasticity value which is softer than the hardest elasticity value in the elastic volume data by the portion of a predetermined value and the elastic volume data having the elasticity value which is softer than the elasticity value of the reference value on the basis of the reference value which is positioned at the elasticity value harder than the softest elasticity value in the elastic volume data by the portion of a predetermined value.

6. The ultrasonic diagnostic apparatus according to claim 1, wherein the 3-elastic volume data grouper is configured to separate the elastic volume data into the hard region, the soft region and the region having the average hardness, on the basis of predetermined values in the elastic volume data.

7. The ultrasonic diagnostic apparatus according to claim 1, comprising an operation unit configured to set a threshold value of the elasticity value, wherein the 3-dimensional elastic image constructor constructs a 3-dimensional elastic image by further separating the elastic volume data which is separated into the hard region and the soft region on the basis of the set threshold value and converting the voxel value of the further separated elastic volume data sets into the voxel value which is larger than the original voxel value at the time of performing volume rendering.

8. The ultrasonic diagnostic apparatus according to claim 7, wherein the threshold value is set based on the characteristic of a histogram of the elasticity value.

9. The ultrasonic diagnostic apparatus according to claim 2, wherein the 3-dimensional elastic image constructor performs coloring on the 3-dimensional elastic image in three dimensions based on the elastic volume data which is separated into the hard region and the soft region using a color bar for 3-dimensional elastic images.

10. The ultrasonic diagnostic apparatus according to claim 9, wherein the 3-dimensional elastic image constructor gives a color which indicates the hardness and a color which indicates the three-dimensionality to the elastic volume data equivalent to the hard region, and a color which indicates the softness and a color which indicates the 3-dimensionality to the elastic volume data equivalent to the soft region, on the basis of the color bars for 3-dimensional elastic images.

11. The ultrasonic diagnostic apparatus according to claim 10, wherein the color bar for 3-dimensional images is set to emphasize black color as the pixel value of the elastic volume data equivalent to the hard region after the rendering decreases and blue color as the pixel value after the rendering increases, and to emphasize black color as the pixel value of the elastic volume data equivalent to the soft region after the rendering decreases and red color as the pixel value after the rendering increases.

12. The ultrasonic diagnostic apparatus according to claim 9, wherein the color bar for 3-dimensional elastic images and a color bar for 2-dimensional elastic images configured to perform coloring on the 2-dimensional elastic image formed by the elasticity values based on the reflected echo signals are set to have different coloring features.

13. The ultrasonic diagnostic apparatus according to claim 1, wherein the display screen displays a preferential display setting providing an indication priority of the first 3-dimensional elastic image and the second 3-dimensional elastic image.

14. An ultrasonic image display method including steps of:
constructing a 3-dimensional image by receiving reflected echo signals and performing volume rendering on elastic volume data; and
displaying the 3-dimensional elastic image on a display screen,
wherein the step of constructing a 3-dimensional elastic image comprises:
grouping the elastic volume data into a first set of elastic volume data of a hard region and a second set of elastic volume data of a soft region by using an elastic value;
volume rendering a first set of elastic volume data to produce a first 3-dimensional elastic image of the hard region;
volume rendering a second set of elastic volume data to produce a second 3-dimensional elastic image of the soft region; and
synthesizing the first 3-dimensional elastic image and the second 3-dimensional elastic image, wherein the synthesizing includes synthesizing the first 3-dimensional elastic image and the second 3-dimensional elastic image to thereby superimpose the first 3-dimensional elastic image and the second 3-dimensional elastic image onto the display screen.

* * * * *